United States Patent
Lithgow

(10) Patent No.: US 9,078,576 B2
(45) Date of Patent: Jul. 14, 2015

(54) NEURAL RESPONSE SYSTEM

(75) Inventor: Brian John Lithgow, Ormond (AU)

(73) Assignee: Monash University (AU)

( * ) Notice: Subject to any disclaimer, the term of this patent is extended or adjusted under 35 U.S.C. 154(b) by 1080 days.

(21) Appl. No.: 12/602,456

(22) PCT Filed: May 30, 2008

(86) PCT No.: PCT/AU2008/000778
§ 371 (c)(1),
(2), (4) Date: Mar. 31, 2010

(87) PCT Pub. No.: WO2008/144840
PCT Pub. Date: Dec. 4, 2008

(65) Prior Publication Data
US 2010/0261978 A1    Oct. 14, 2010

(30) Foreign Application Priority Data

May 31, 2007    (AU) ................................ 2007902924

(51) Int. Cl.
 *A61B 5/04*    (2006.01)
 *A61B 5/0484*    (2006.01)
 *A61B 5/00*    (2006.01)

(52) U.S. Cl.
CPC ......... *A61B 5/04017* (2013.01); *A61B 5/04001* (2013.01); *A61B 5/0484* (2013.01); *A61B 5/6815* (2013.01); *A61B 5/6838* (2013.01)

(58) Field of Classification Search
USPC ................................................ 600/544, 545
See application file for complete search history.

(56) References Cited

U.S. PATENT DOCUMENTS

| 4,794,533 | A | * | 12/1988 | Cohen | 600/544 |
| 5,447,166 | A | * | 9/1995 | Gevins | 600/544 |
| 5,846,207 | A | * | 12/1998 | Rosenfeld | 600/544 |
| 2003/0013981 | A1 | * | 1/2003 | Gevins et al. | 600/544 |
| 2007/0208263 | A1 | * | 9/2007 | John et al. | 600/509 |

FOREIGN PATENT DOCUMENTS

WO    WO 2006/024102    3/2006

OTHER PUBLICATIONS

Garrett A. et al. "Electrovestibulography: The "DC" Potential Used to Separate Meniere's Disease and Benign Paroxysmal Positional Vertigo." *IEEE Engineering in Medicine & Biology Society, 29th Annual International Conference.* 2007. pp. 2381-2384.
Hall, James W. III. "Handbook of Auditory Evoked Responses." 1992.
Shoushtarian M. et al. The Relationship Between Electrovestibulography and Parkinson's Disease Severity. *IEEE Engineering in Medicine & Biology Society, 29th Annual International Conference.* 2007. pp. 2377-2380.

* cited by examiner

*Primary Examiner* — Etsub Berhanu
(74) *Attorney, Agent, or Firm* — Merchant & Gould P.C.

(57) ABSTRACT

A neural response system, including a plurality of filters for each receiving and filtering a plurality of tilt response signals obtained from a person; a segmenter for segmenting the filtered response signals into time segments; and a neural event extractor for performing a neural event extraction process on each of the time segments to obtain and generate biomarker data representing a plurality of biomarkers for each segment.

39 Claims, 13 Drawing Sheets

NEURAL RESPONSE SYSTEM

This application is a National Stage Application of PCT/AU2008/000778, filed 30 May 2008, which claims benefit of Serial No. 2007902924, filed 31 May 2007 in Australia and which application(s) are incorporated herein by reference. To the extent appropriate, a claim of priority is made to each of the above disclosed applications.

FIELD

The present invention relates to a neural response system that can provide biological data indicative of a number of disorders using electrovestibulography.

BACKGROUND

Systems have been developed to obtain an auditory evoked response (AER) or brainstem auditory evoked response (BAER) for a patient representing activity of the patient's auditory system. The AER is an electrical brain wave or neural response obtained from electrodes placed on the patient in response to a stimulus, normally a sound. Depending on the latency of the response and the placement of the electrodes, different classes or types of AERs can be obtained. Those with the shortest latency are generated by the inner ear and the auditory nerve, and are referred to as electrocochleography ("ECOG" or "ECochG") responses. The next response reflects activity within the auditory brainstem and is referred to as an auditory brainstem response (ABR). Further detail is provided in Hall, James W, III; Handbook of Auditory Evoked Responses; Allyn and Bacon; Needham Heights, Mass., 1992.

Electrocochleography systems are currently used to perform diagnoses of the cochlea and vestibular apparatus. In the case of the vestibular system, recently analysis for this specific part of the ear has been referred to as electrovestibulography (EVestG), being a distinct variant of ECOG. The systems are used to produce a patient neural response which involves placing a recording electrode as close as practical to a patient's cochlea. An acoustic transducer, eg an earphone, is used to provide an auditory stimulus to evoke the response. For EVestG the patient is however tilted, in different directions, to evoke a specific response from the vestibular apparatus. It is not necessary to also use an auditory stimulus for EVestG. A distinct EVestG signal, similar to an ECOG signal but representing the neural response from the vestibular apparatus, is used to determine an Sp/Ap ratio that can be used for the diagnosis of a number of conditions, particularly Meniere's disease. The first wave, normally labelled N1, of the response signal is examined to determine the summating potential (Sp), the action potential (Ap) and the second summating potential (Sp2), as shown in FIG. 1. The response is only of the order of a few µV and is received with considerable unwanted noise making it difficult to determine and isolate.

International patent publication WO 2006/024102 to Monash University describes an ECOG system to extract neural event data that can be used to indicate whether a person has Meniere's, Parkinson's disease or depression. The system produces biological marker data representing the Sp/Ap ratio and a TAP marker that can be used to indicate the presence of a disorder. To assist with identification of a wide variety of neurological and neurodegenerative disorders it would be advantageous to provide at least a useful alternative or in particular a system that is able to provide additional biological marker data for a person that can be used for different disorders.

SUMMARY

In accordance with the present invention there is provided a neural response system, including:
 a plurality of filters for each receiving and filtering a plurality of tilt response signals obtained from a person;
 a segmenter for segmenting the filtered response signals into time segments; and
 a neural event extractor for performing a neural event extraction process on each of the time segments to obtain and generate biomarker data representing a plurality of biomarkers for each segment.

The present invention also provides a neural response process, including:
 receiving and filtering, using a plurality of filters, a plurality of tilt response signals obtained from a person;
 segmenting the filtered response signals into time segments; and
 processing each of the time segments to obtain and generate biomarker data representing a plurality of biomarkers for each segment.

The present invention also provides a neural response system, including:
 a neural response processor for processing time segments of tilt response signals obtained from a person to obtain biomarker data representing a dynamic phase of each tilt response signal; and
 a diagnostic tool for processing the biomarker data to determine whether said person has a neurological condition.

BRIEF DESCRIPTION OF THE DRAWINGS

Preferred embodiments of the present invention are hereinafter described, by way of example only, with reference to the accompanying drawings, wherein.

DETAILED DESCRIPTION

Figure 1:
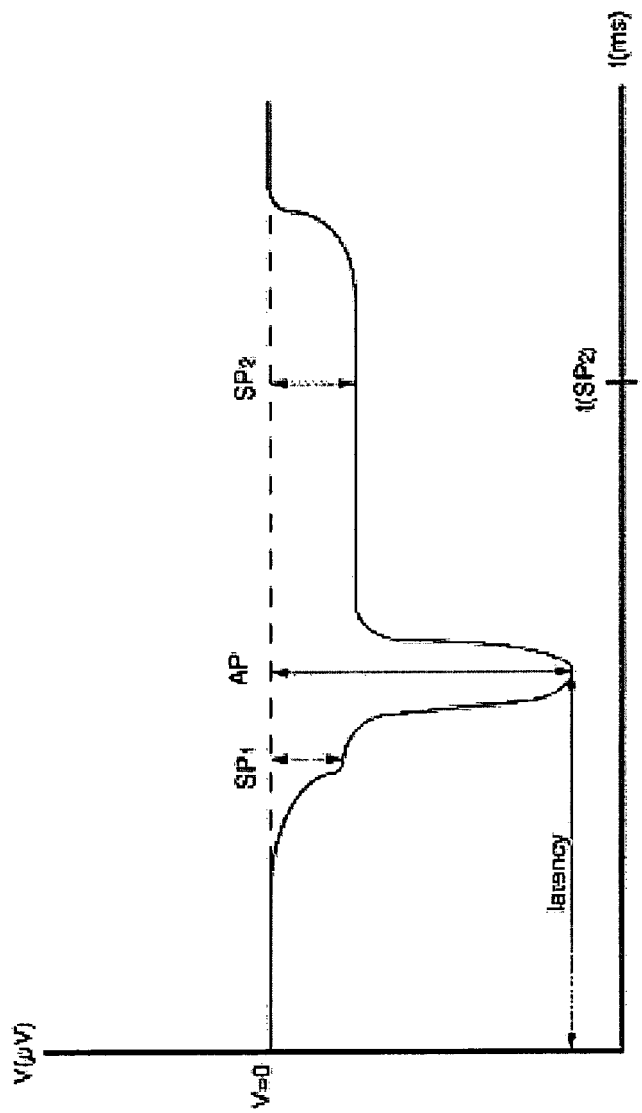
FIG. 1 is a representation of Sp, Ap and Sp2 points related to the first wave of a generalized ECOG response signal from an ECOG system and defines the summating potentials Sp and Sp2 and the action potential Ap.
Figure 2:
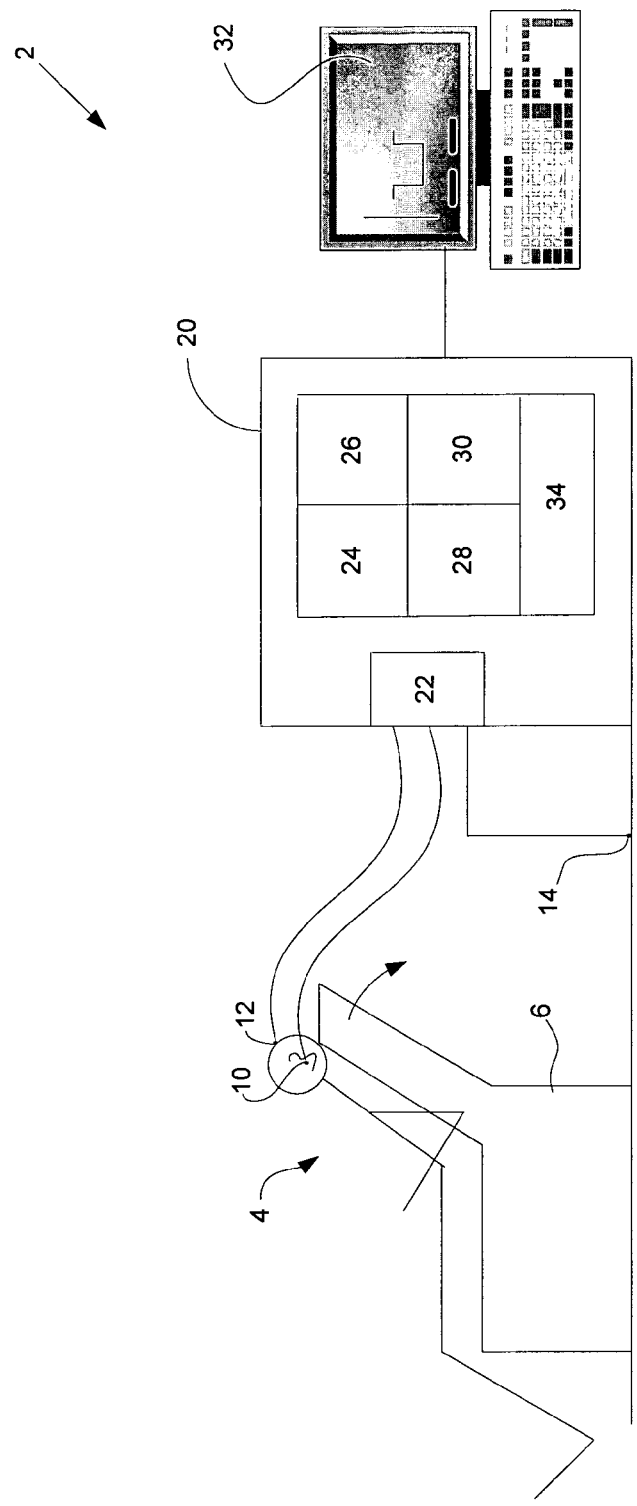
FIG. 2 is a schematic diagram of a preferred embodiment of an EVestG system connected to a patient.

An electrovestibulography (EVestG) system 2, as shown in FIG. 2, provides a neural response system that is able to generate a biological marker, or biomarker, data representing over 5,000 biomarker measures from a patient 4 subjected to involuntary tilt movements in a tilt chair 6. The biomarker data is generated by signal processing analysis of EVestG signals produced in response to the stimulus provided by the involuntary tilts.

An EVestG signal is obtained from electrodes 10, 12 and 14 electrically connected to an amplifier circuit 22 of a computer system 20 of the system 2. A first electrode 10 (eg a ECochG Electrode produced by Bio-Logic Systems Corp (http://www.blsc.com/pdfs/HearCatalog.pdf) is placed on the tympanic membrane of an ear of a patient 4. A second electrode 12 is placed on the patient's earlobe, as a reference point, and a third electrode 14 is connected to the patient's forehead and to the common point of the amplifier. A shield connection 16 is also made to an electrical isolation shield 18 normally placed around the testing room. The shield 18 is connected to the shield of the amplifier 22. The testing room is a sound attenuated booth. The booth may include the amplifier 22 with the rest of the computer system 20 placed outside the booth and connected to the amplifier 22 by a USB connection.

The patient 4, as shown in FIG. 2, is placed on the chair 6, such as a recliner lounge chair, that allows the patient's head to rest passively and supported securely to relax the subject during the testing cycle. Electrically powered tilt chairs have been specifically produced by Neuro Kinetics Inc. (http://www.neuro-kinetics.com) that enable a patient to be tilted and produce a response to this stimulus which is less corrupted by muscle artefact. An involuntary head tilt can be obtained by an assistant manipulating the chair 6 so as to induce the head tilt without any patient neck muscle activity. Alternatively, the tilt chair can be fitted with and controlled by hydraulic components to invoke a predetermined set of involuntary tilt sequences.

A hydraulically actuated chair is used and configured to ensure stray electric fields caused by the actuation of electrical servo-motors are eliminated as far as possible from being generated in the testing booth. The hydraulically actuated chair is used to provide the tilts without producing either neck muscle artefacts or stray electric fields that may corrupt sensitive signal measurements. To reduce ocular artefacts, the patient is also asked to keep their eyes closed during the testing cycle. The head is tilted down to approximately the same angle as a maximum voluntary head tilt that can be achieved by the patient themself. An EVestG signal or tilt response is obtained for each tilt sequence. The tilts, or tilt sequences, are up/down (patient upright and prone), forward/back, ipsilateral, contralateral, and rotation (patient upright and prone).

Figure 3:
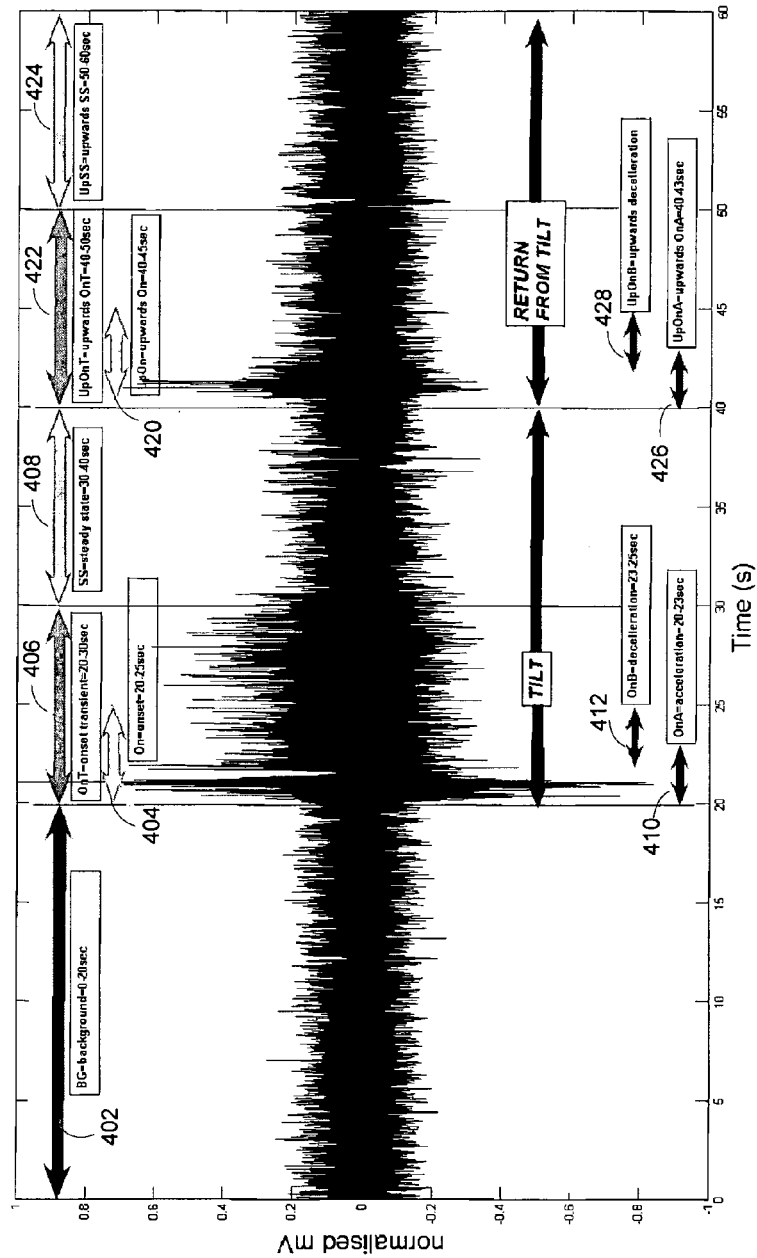
FIG. 3 is a representation of the raw data for an EVestG signal produced by a tilt sequence of the system.

The tilts each produce a raw EVestG response signal, as shown in FIG. 3. The tilt sequences performed by the chair 6 are controlled so that the EVestG response signal obtained is divided into 15 time epochs or segments, but this can be reduced or increased. The neural response produced on electrodes 10 to 14 is continuously recorded by the system 2. The EVestG neural response signal for each tilt is a time domain voltage signal having multiple frequency components. The main components of interest are up to 22,500 Hz. In particular the Sp peak (depending on the signal to noise ratio (S/N)) is only a few samples wide. Accordingly a sampling rate of 44.1 kHz is required during the test cycle as this rate has sufficient sensitivity to recognise and record this event with adequate accuracy by the system 2. This sampling rate can be higher than 44.1 kHZ, and the system 2 would then require faster signal processing components. The seven tilts are performed with two sets of electrodes 10 to 14 positioned respectively for the left ear of the patient and the right ear of the patient. This provides left and right data simultaneously for each ear for each of the seven tilts. Both ears are tested in both dynamic and static phases of all tilt manoeuvres, as a neurological disorder can exist in either hemisphere of the brain, and may only reveal its presence by comparison of each sides response in similar excitatory or inhibitory phases of one or other of the left and right vestibular apparatus. Such versatility is required if the diagnostic test is to recognise differences in evoked response between each hemisphere of the brain, where in some neurological disorders asymmetry of functioning can occur, (e.g. as for Parkinson's disease).

The sequence for each tilt is to record firstly for 20 seconds with the patient in the tilt chair resting the head/neck against a neck rest and recording a background (BG) signal segment 402 for t=20 seconds. This segment 402 includes a BGi segment which is 1.5 seconds immediately prior to the occurrence of tilt. The patient is then tilted through 45° to come to rest after 2 to 3 seconds. This gives an onset (On) segment 404 for t=20-25 seconds, an onset transient (OnT) segment 406 for t=20-30 seconds, and steady state (SS) segment 408 for t=30-40 seconds. The semicircular canals of the ear function to detect the onset of head movement, and by analysing approximately 5 seconds from a signal recorded at the onset of the head tilt (the On segment) assists with determining the response generated by the semicircular canals. The onset response includes two additional segments, the movement (OnA) segment 410 and the post movement (OnB) segment 412, which occur at t=20-23 seconds and t=23-25 seconds respectively. The OnA segment 410 can be divided to provide an additional OnAA segment 413 for the first 1.5 seconds after tilt and an OnBB segment 415 for the next 1.5 seconds after tilt. The OnAA and OnBB segments are selected to be 20-21.5 and 21.5-23 seconds respectively for increased separation of the acceleration and deceleration components that these segments respectively represent. The times are selected to take into account latency of the hydraulic chair 4 of 0.6-0.8 sec. These segments include responses produced by the semicircular canals and the otolithic organs. The driven semicircular canal response ceases after about 10 seconds, and accordingly the first 10 seconds are therefore considered as the onset transient (OnT) where this decay is observed. The otolith organs, on the other hand, function to maintain static balance, or balance during steady unidirectional movements. The steady state (SS) segment 408 can therefore be analysed to provide the driven response of the otolithic organs separately.

The sequence for the tilt is completed at t=40 seconds by then returning the patient to the original position. The patient is returned to the original position over 1 to 2 seconds and the response produced can again be segmented in a similar manner. The segments for the return part of the tilt sequence:

(i) Upwards Onset (UpOn) 420 for t=40-45 seconds;
(ii) Upwards Onset Transient (UpOnT) 422 for t=40-50 seconds;
(iii) Upwards Steady State (UpSS) 424 for t=50-60 seconds;
(iv) Upwards Acceleration (UpOnA) 426 for t=40-43 seconds;
(v) Upwards Deceleration (UpOnB) 428 for t=43-45 seconds;

(vi) UpOnAA 427 for t=40-41.5 seconds; and
(vii) UpOnBB 429 for t=41.5-43 seconds.

The upOnAA segment is selected to be 40-41.5 seconds for increased separation of the acceleration component, and the upOnBB segment to be 41.5-43 seconds for increased separation of the deceleration component. Again the times are selected to take into account hydraulic chair latency of 0.6-0.8 sec.

The seven tilt sequences, or tilts, are:
(i) Up/Down. The chair 6 is moved so as to accelerate the patient's body vertically with patient's head in a normal upright position, and then returned.
(ii) Up/Down Prone. The chair is moved so as to accelerate the patient's body vertically with the patient's head and body in a prone or lying down position, and then returned.
(iii) Forward/Back. The patient's body is tilted from a rest position backwards through 45°, and then returned.
(iv) Ipsilateral. The patient's body is moved through 45 degrees ipsilaterally to the electrode 10, and then returned: If the electrode 10 is in the left ear the tilt is to the left then the tilt is back to the right. For the right ear the tilt is to the right.
(v) Contralateral. The patient's body is moved 45 degrees contralaterally to the electrode 10, and then returned. For instance, if the electrode 10 is in the left ear, the tilt is to the right and the patient is returned. For the right ear the tilt is to the left.
(vi) Rotation. The patient's body is rotated between 45 and 90 degrees to the right, and then returned, with patient's head in a normal upright position.
(vii) Rotation Prone. The patient's body is rotated between 45 and 90 degrees to the right, and then returned, with the patient's body in a prone or lying down position.

During all movements the head and neck are not moved relative to the body. The whole body is moved to reduce muscle artefacts. Alternatively, the tilts may be performed by having the subject lie down on their back and tilting their body through ipsilateral, contralateral, vertical and backward directions. These tilts produce less muscle artefacts particularly for the ipsilateral and contralateral tilts.

Figure 4:
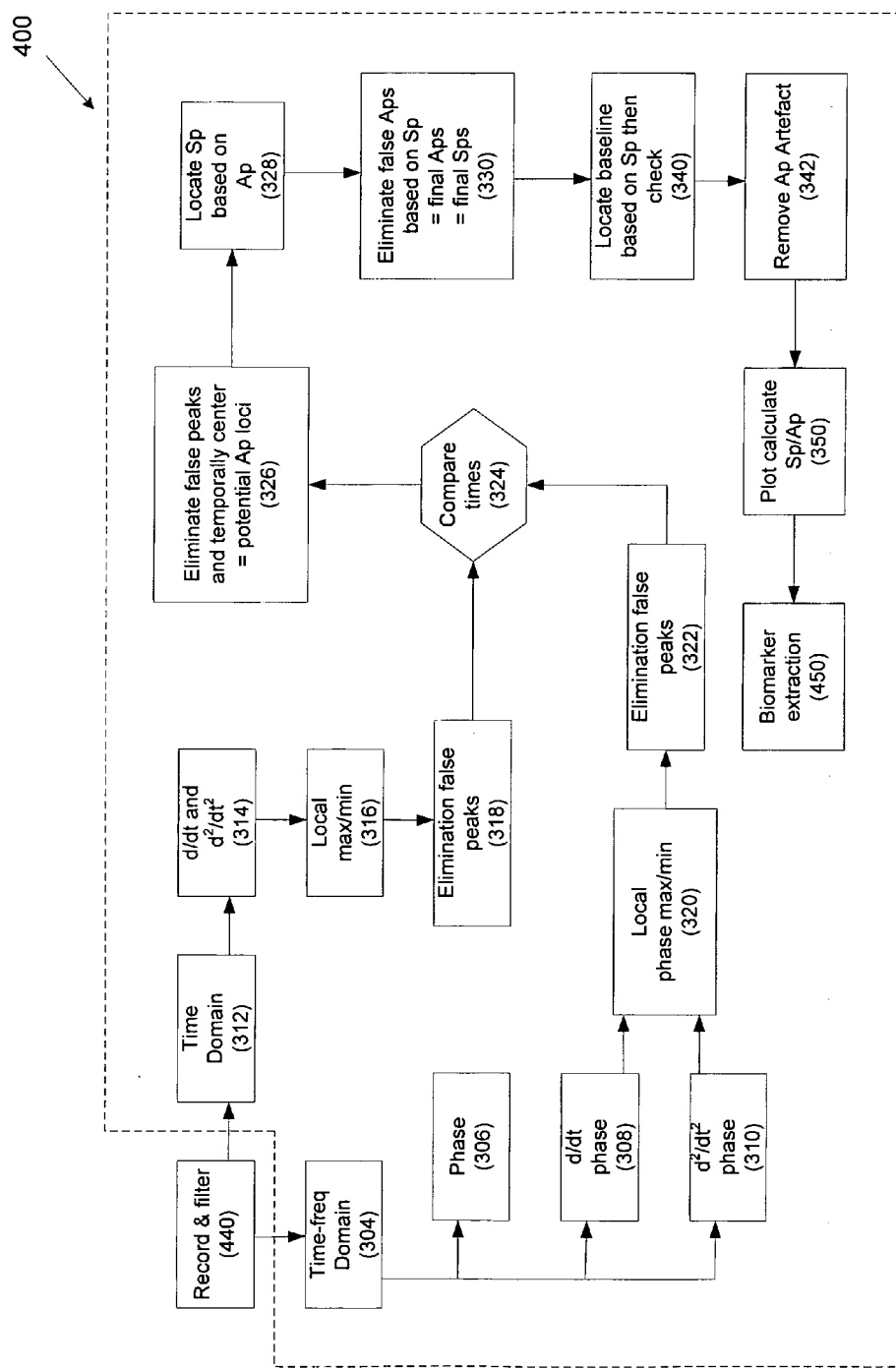
FIG. 4 is a diagram of a neural event extractor and a neural event extraction process performed by an analysis module of the system.

The computer system 20 of the EVestG system 2 includes the amplifier circuit 22 and a communications module 24 for handling the data output of the amplifier 22 and then storing the response as a voltage signal over time as a wave file using a computer program such as Adobe Audition (http://www-.pacific.adobe.com/products/audition/main.html) provided by a capture module 26. The amplifier 22 includes a CED 1902 isolated pre-amplifier circuit and a CED Power 1401 analogue to a digital converter (ADC). Both the CED 1902 and CED 1401 ADC are produced by Cambridge Electronic Design Limited (http://www.ced.co.uk). The CED 1401 ADC has an excellent low frequency (less than 1 Hz) response. The computer system 20 further includes an analysis module 28 and a display module 30. The analysis module 28 provides a neural event extractor 400 and includes computer program code (eg. MATLAB® code, http://www.mathworks.com) responsible for performing a neural event extraction process (NEEP) of the extractor 400, as shown in FIG. 4, in conjunction with the other software modules. The analysis module 28 also provides a number of different filters used to filter the response signal samples, as discussed below. This filtering may include the removal of the system (or White Noise) response of the feature detection components of the neural event extraction process.

Figure 6:
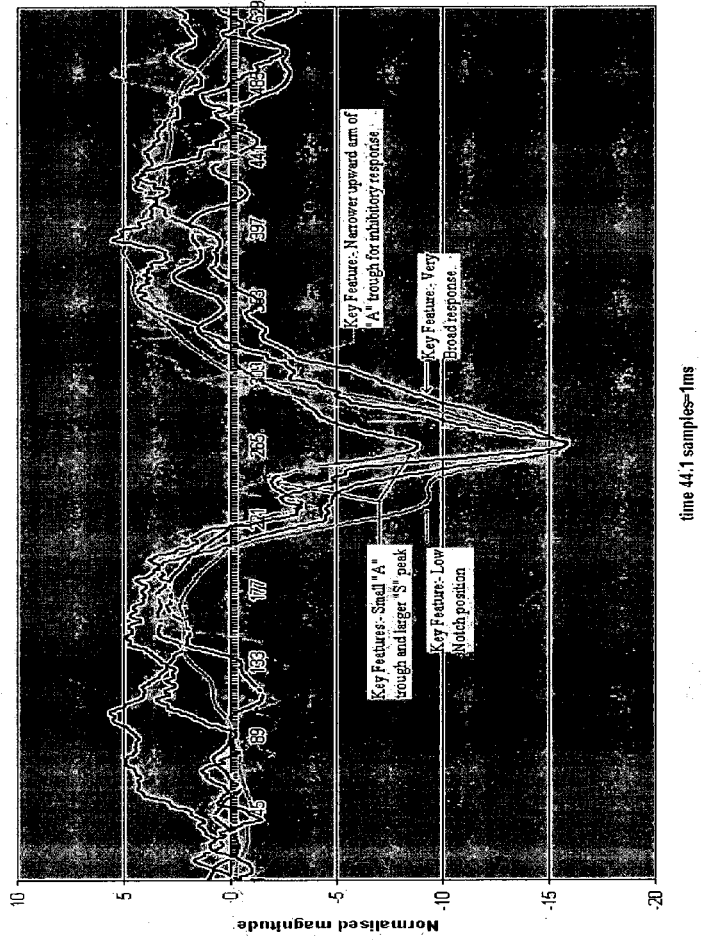
FIG. 6 is a diagram of a Sp/Ap curve generated by the system.

The graphics display module 30 generates a user interface 32 for an operator of the system 2 to provide input controls so that the operator can control the neural event extraction process (NEEP), and to generate displays of neural event data, such as the Sp/Ap plot shown in FIG. 6. The computer program code of the software modules 24 to 30 are stored on memory of the computer system 20 and are run on an operating system 34, such as Microsoft Windows or Linux. The hardware used may include the amplifier circuit 22 and a standard personal computer 20, such as that produced by IBM Corporation (http://www.ibm.com). ECOG recording systems are produced by Bio-Logic Systems Corp (http://www-.blsc.com/hearing/). Whilst the neural event extraction process (NEEP) may be performed under the control of the software of the modules 24 to 34, it will be understood by a skilled addressee that steps of the process can be performed by dedicated hardware circuits, such as ASICs and FPGAs, and also performed by components or modules distributed across a computer communications network, such as the Internet. For example, dedicated filter circuits can be used to provide the filters, and dedicated digital signal processors (DSPs) can be used to perform a number of the signal processing steps to enhance the processing speed.

Figure 5:
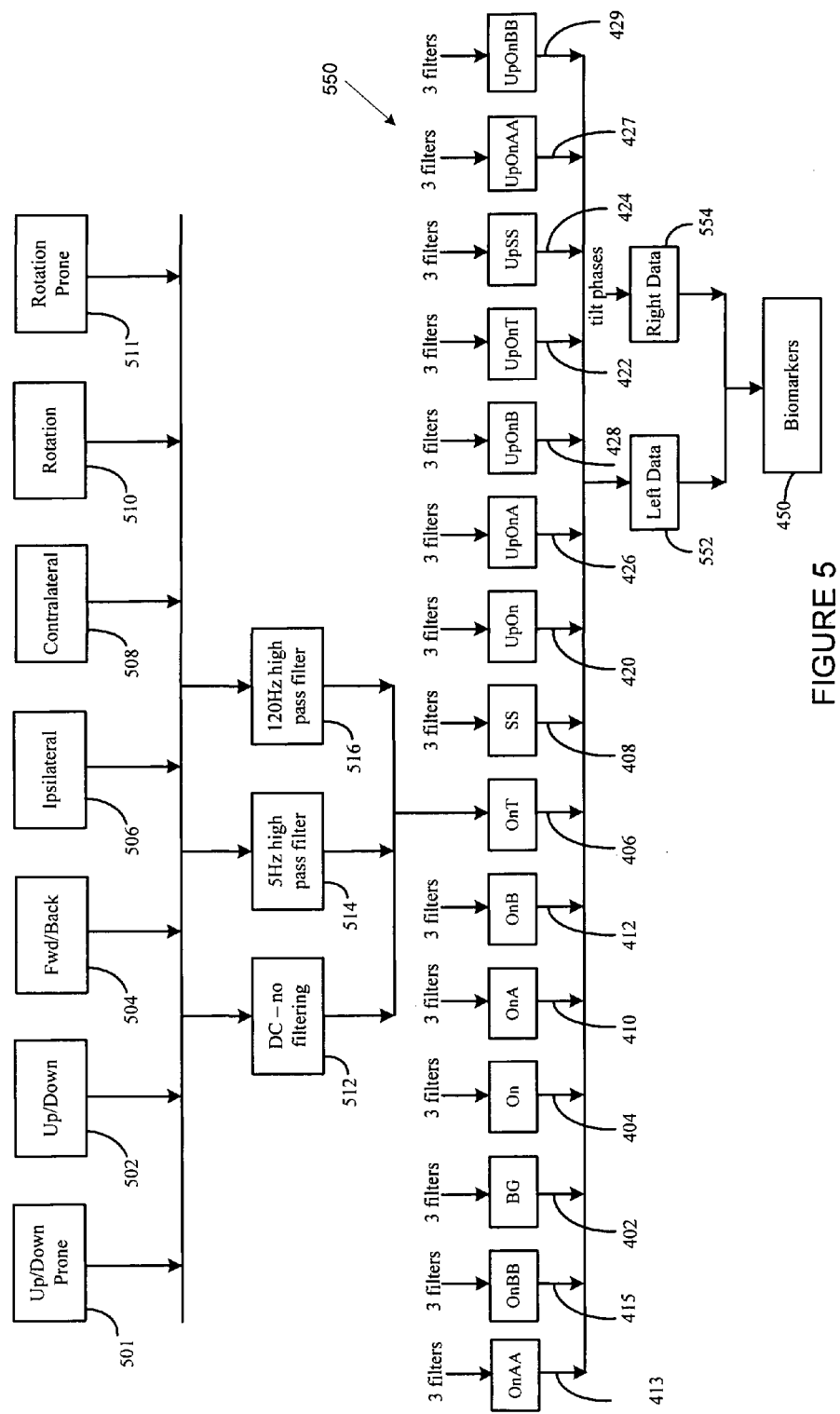
FIG. 5 is an architecture diagram of filters and a segmentation component of the system.

The neural event extraction process (NEEP), as shown in FIG. 4, is the same as that described in WO 2006/024102 for an EvestG response, except for the recording filtering, and segmenting process 440, and the biomarker extraction process 450. The data representing the EVestG responses obtained from each of the seven tilts and for each ear of a patient, i.e. 14 responses, is recorded, as discussed above, and then filtered three different ways to provide filtered data for three filtered responses for each tilt response, i.e. filtered response data for 42 filtered tilt responses. A shown in FIG. 5, the tilt responses of each tilt 501, 502, 504, 506, 508, 510 and 511 are each filtered by a first filter 512, a second filter 514 and a third filter 516. The first filter 512 provides no filtering, as it allows all frequencies to pass, including the data representing DC voltage levels. It does, however, include a very narrow notch filter which introduces no phase shifts but removes power line harmonics, e.g. at 50 Hz or 60 Hz, and also removes hydraulic (proportional valve) switching artefacts that may be introduced by hydraulic actuation of the chair. This notch filter is also employed at the output of the second and the third filters 514 and 516. The second and third filters 514 and 516 both provide high pass filtering. The second filter 514 includes a 5 Hz high pass filter and the third filter 516 includes a 120 Hz high pass filter. Providing the three filtered tilt responses produced by the filters 512, 514 and 516 for processing by a neural event extraction process (NEEP) gives the benefit that groups of biological markers that can be corrupted by low frequency data are enhanced in the high pass filtered responses, whereas other critical biological markers that are only present or can only be extracted when the low frequency data is present are also available, e.g. the biological markers used for Meniere's disease.

The 42 filtered tilt responses are each segmented by a segmentation process 440 performed by segmenter 550 of the module 28 in order to produce the fifteen segments 402, 404, 406, 408, 410, 412, 413, 415, 420, 422, 424, 426, 427, 428 and 429 for each filtered tilt response, as discussed above. This produces 630 sets of data representing 630 filtered tilt response segments. The segments comprise data obtained form the left ear of the patient 552 and data obtained from the right ear of the patient 554. The output of the record, filter and segmentation process 440 is the 630 filtered tilt response signals that are each then subjected to the remaining processes of the neural event extraction process (NEEP) shown in FIG. 4. This produces Sp/Ap data for each segment, i.e. for each of the 630 sets of data. The segments are each treated as an EVestG response by the neural event extraction process (NEEP). As discussed in WO 2006/024102, the process decomposes each response segment using a complex Morlet wavelet to obtain phase data across seven equally logarithmically space scales from 600 Hz to 12 KHz. The scale data is processed to determine loci where sharp changes in phase occur across all scales.

However, a large phase change may be indefinable across the scales but at more than one (or slight variations in) sample time. At scale 1, for example, a locus could be found at say time sample 344. For scale 2 the loci might be at scale 345, scale 3 at loci 347, scale 4 loci 349, scale 5 loci 346, scale 6 loci 345 etc. This represents a curved connection of points across the scales relating the same phase change. To cater for this the NEEP allows for and applies an acceptable gap between scale sample times. This gap may be arbitrarily set, but is typically 1 to 3 samples.

Once these loci are discriminated, characteristic data for a Sp/Ap plot is derived and used to select neural responses from artefacts. The data for a Sp/Ap curve is determined by averaging the loci determined across the scales, and an EVestG plot can be produced from the data for each segment as shown in FIG. 6.

The neural event extraction process (NEEP) can inadvertently detect loci due to White noise. To address this and improve the S/N ratio of the extracted EVestG Sp/Ap plot the white noise response can be subtracted by the system 2. The system 2 achieves this by first inputting white noise filtered to match the recording characteristics of the system (eg. 10 kHz low pass and no (DC), 5 or 120 Hz high pass filtering) and recording the EVestG Sp/Ap system response to this input, which is stored as a Band Limited White Noise (BLWN) response. A scaled BLWN response is then subsequently subtracted from the EVestG (RAEVestG) produced by the NEEP. The scaling factor is decided by determining the Ap point of the RAEvestG. The scaling factor is set to 0 and incremented in 0.01 steps until the Output data=RAEVestG minus the scaled BLWN response sees the Ap point (response plot minima) shifting by more than an arbitrary time, typically 2 samples. Once subtracting the scaled BLWN response causes a marked adjustment in the position of the Ap point, the scaling factor (scale) is set and not increased any further. This gives an adjusted NEEP Output EVestG=RAEVestG-scale*BLWN. The BLWN response is produced by the NEEP processing the white noise response with the threshold in step 318 set so that significant field potentials are detected to characterise the BLWN response.

Sometimes neural events (field potentials) occur so that their waveforms overlap. When this occurs the diagnostic biomarkers can become corrupted. To solve this problem the neural event extraction process (NEEP) can exclude such events without loss of biomarker integrity. To find these events the loci of the Ap points are determined. If these loci are closer than an arbitrary number of samples typically 66 samples (1.5 ms) both field potentials can be excluded. A flag can be set or reset so that the exclusion decision can be switched in or out as part of the NEEP processing.

Figure 7:
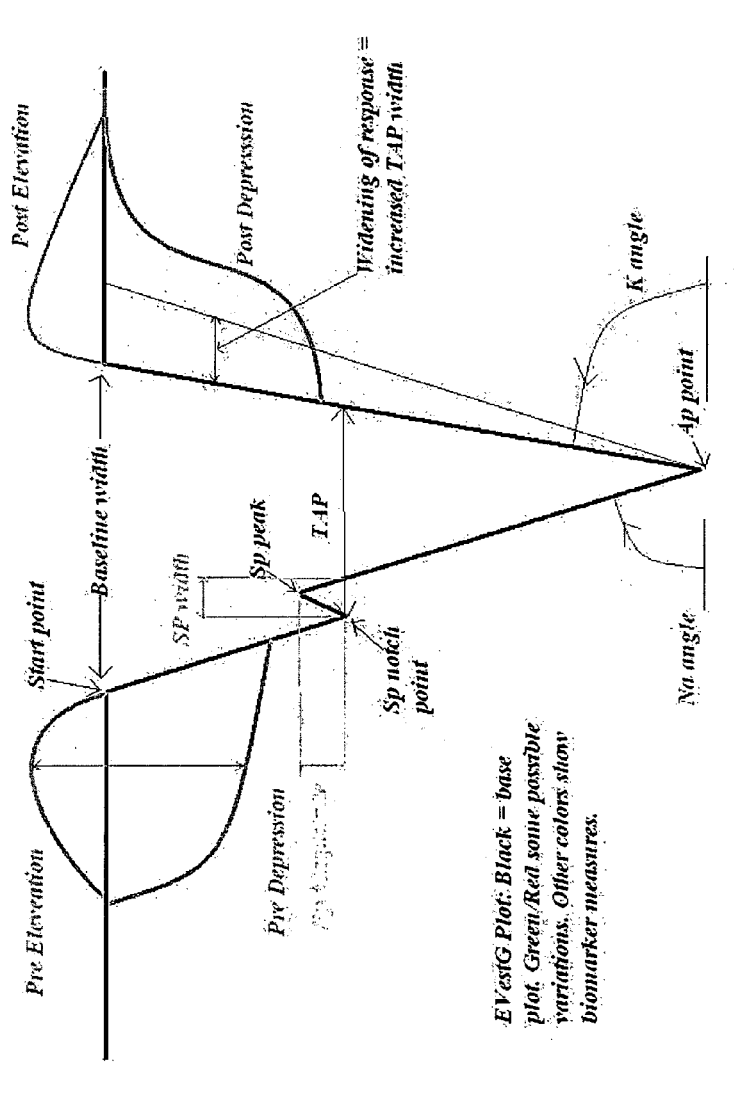
FIG. 7 is a schematic diagram of biomarkers obtained from data of an EVestG plot.

Once the Sp/Ap or EvestG curve data is produced for each segment (350), the extraction process is able to invoke a biomarker extraction process (450) on each segment that generates metric data or biological marker data representing 17 different biological markers. As there are 630 different segments produced for each patient, this gives rise to biological marker data representing 630 measures of each biomarker. Accordingly, the biomarker data for each patient represents 10,710 biomarker measures. This is a considerable amount of data obtained from one patient subjected to the seven tilt sequences and can be used to accurately determine the presence or not of a wide variety of neurological and neurodegenerative disorders. The 17 biological markers are as defined below and illustrated in FIG. 7 (and given the definitions Ap is the whole V shaped EVestG curve; and the Ap point is the lowest point of the Ap plot):

(i) Pre Ap Elevation or Depression. An elevation or depression above/below the baseline immediately preceding the Ap.

(ii) Post Ap Elevation or Depression. An elevation or depression above/below the baseline immediately after the Ap.

(iii) Ap Magnitude. The voltage magnitude at the Ap point.

(iv) Sp notch point (loci). The time at which the downward arm of the Ap reverses/slows/stops, typically about 0.3 ms after Ap onset.

(v) Start point (loci). The time of commencement of the Ap.

(vi) Baseline width. The width of the Ap at the baseline level.

(vii) Sp peak. The tip of the short rise after the Sp notch point before the continuation downwards of the Ap towards the Ap lowest point.

(viii) Sp width. The width (time) from the Sp notch to the next downward arm of the Ap.

(ix) Sp Magnitude. The height of the Sp peak above the Sp notch point.

(x) TAP (internal). The width (time) of the Ap at the Sp notch level measured from the downward arm of the Ap after the Sp notch horizontally to the upward arm of the Ap.

(xi) TAP (notch). The width (time) of the Ap at the Sp notch level measured from the Sp notch horizontally to the upward arm of the Ap.

(xii) Na angle. The angle of the downward arm of the AP between the Ap lowest point and the height of the Sp notch measured from vertical to that arm.

(xiii) K angle. The angle of the upward arm of the AP between the Ap lowest point and the height of the Sp notch measured from vertical to that arm.

(xiv) Na+K angle. Sum of the eleventh and twelfth biomarker values.

(xv) Sp/Ap ratio. Vertical distance from Sp notch to baseline divided by vertical distance from Ap point to baseline.

(xvi) Spike Rate. The number of field potentials detected and used to form the Ap plot.

Figure 12:
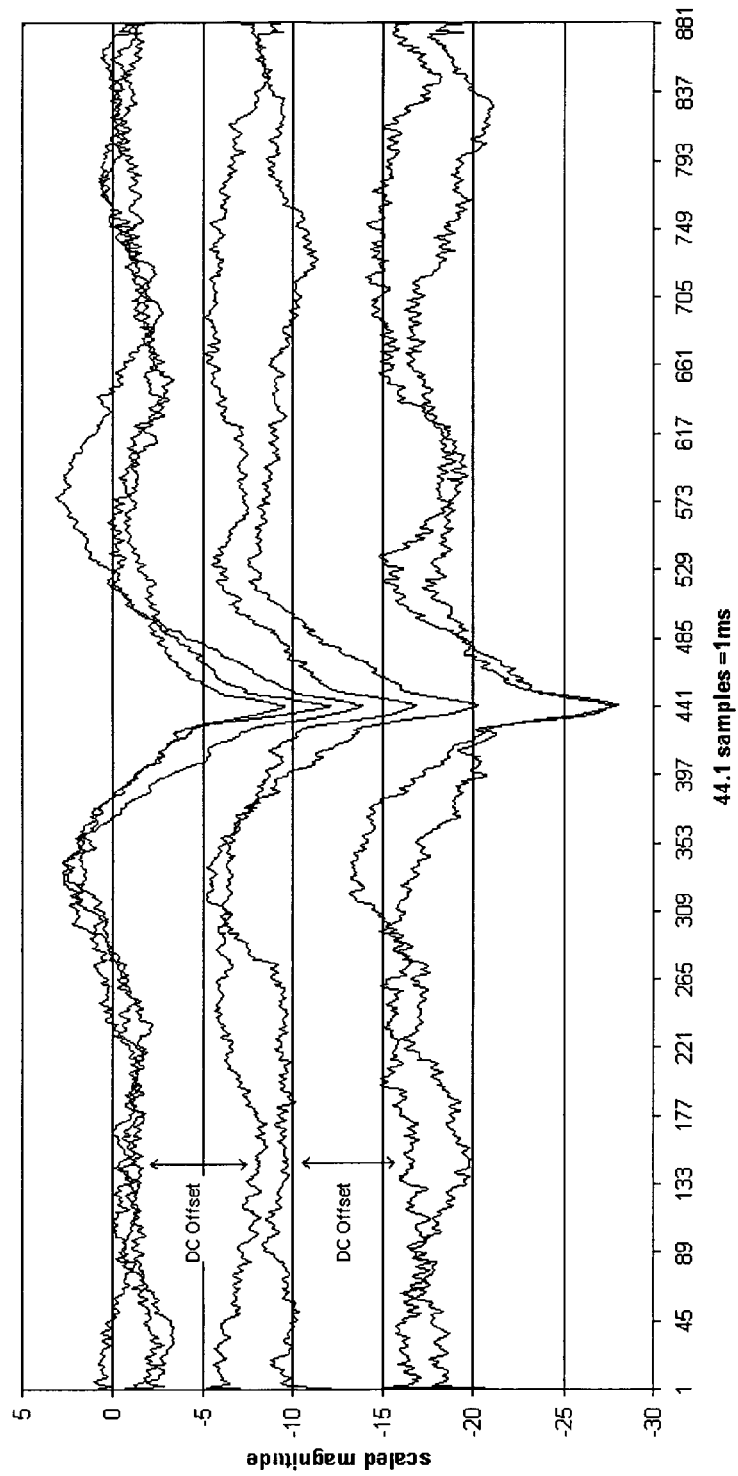
FIG. 12 is a diagram of a Sp/Ap curve generated by the system showing distinct DC shifts for a subject suffering from Meniere's disease.
Figure 13:
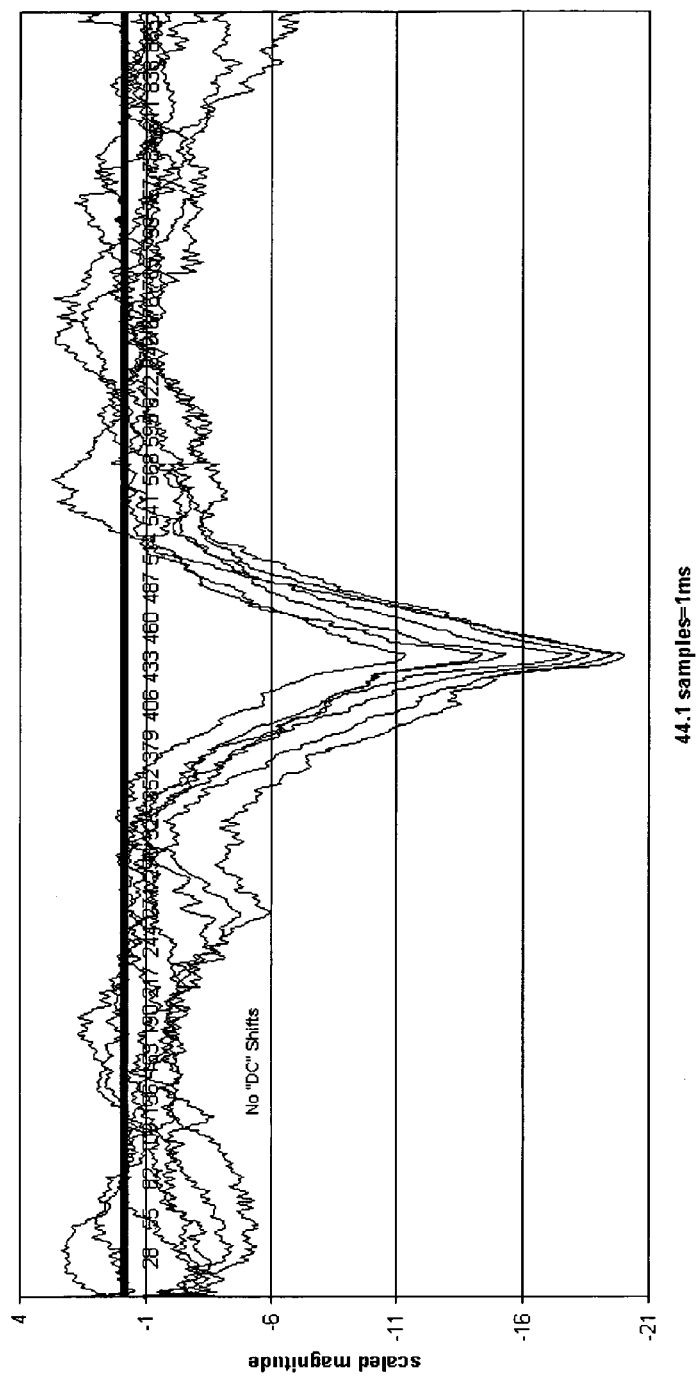
FIG. 13 is a diagram of a Sp/Ap curve generated by the system showing a lack of DC shifts for a subject with BPPV.

(xvii) DC Shift. The vertical shift between different Ap plots measured from the baseline level, as shown in FIGS. 12 and 13.

An additional two biomarkers for each of the 42 filtered tilt response signals is obtained by subtracting the data obtained in the OnAA and OnBB segments from the BGi segment for each response signal. This produces:
(a) BGi=OnAA response data, and (b) BGi=OnBB response data.

This produces 84 additional biomarkers representing the dynamic response of each of the respective tilt response signals.

Figure 8:
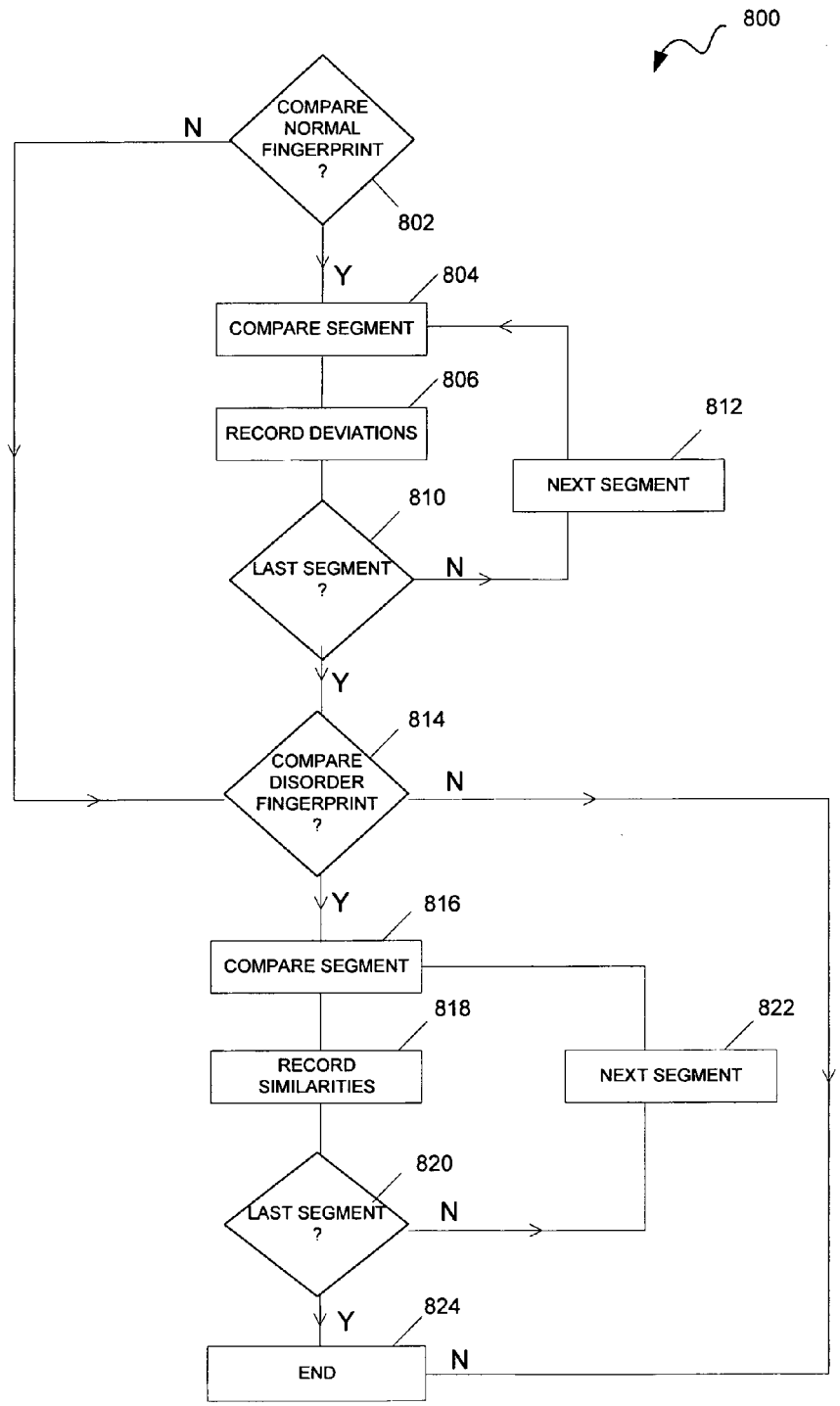
FIG. 8 is a diagram of a diagnostic tool and process of the system.

The analysis module 28 also provides a diagnostic tool 800 which performs a diagnostic process, as shown in FIG. 8, for a number of different disorders. The diagnostic process for each disorder involves first determining (based on a processing control data) whether the biological marker data for a patient is to be compared with that of fingerprint biological marker data for a normal person without the disorder (802). If not, the process proceeds to step 814, but otherwise if it is to be so compared, then the biological marker data for a first recorded segment is compared with the normal fingerprint data (804). The comparison is a statistical process that looks for deviations, and any deviations obtained from the fingerprint biomarkers are recorded as biomarker deviations for that particular biomarker. Step 810 determines whether the last $630^{th}$ segment has been processed, and if not, the biological marker data for the next segment (812) is accessed and the comparison process performed (804). The deviation data can be recorded as a log at step 806 or simply a sum maintained of the number of deviations for a particular biomarker. Once all the 10,710 biomarker measures have been compared, a determination is made at step 814 as to whether the biomarker data needs to be compared with fingerprinted biological marker data for a person having the disorder. If so, then a similar comparison process is performed, where the biological marker data for the first segment is accessed and compared with the disorder fingerprint data (816). Again, a statistical analysis process is performed, but this time to determine and record similarities between the biological markers for each segment (818). Biological marker data for the patient that is similar to that of the disorder segment is recorded, again as a data log or by simply summing the similarities for each biomarker. Once the last segment (the $630^{th}$ segment) has been accessed, as determined at step 820, the process then ends (824), otherwise the next segment is accessed (822) and the comparison process 816 and recording process 818 completed again.

Figure 9:
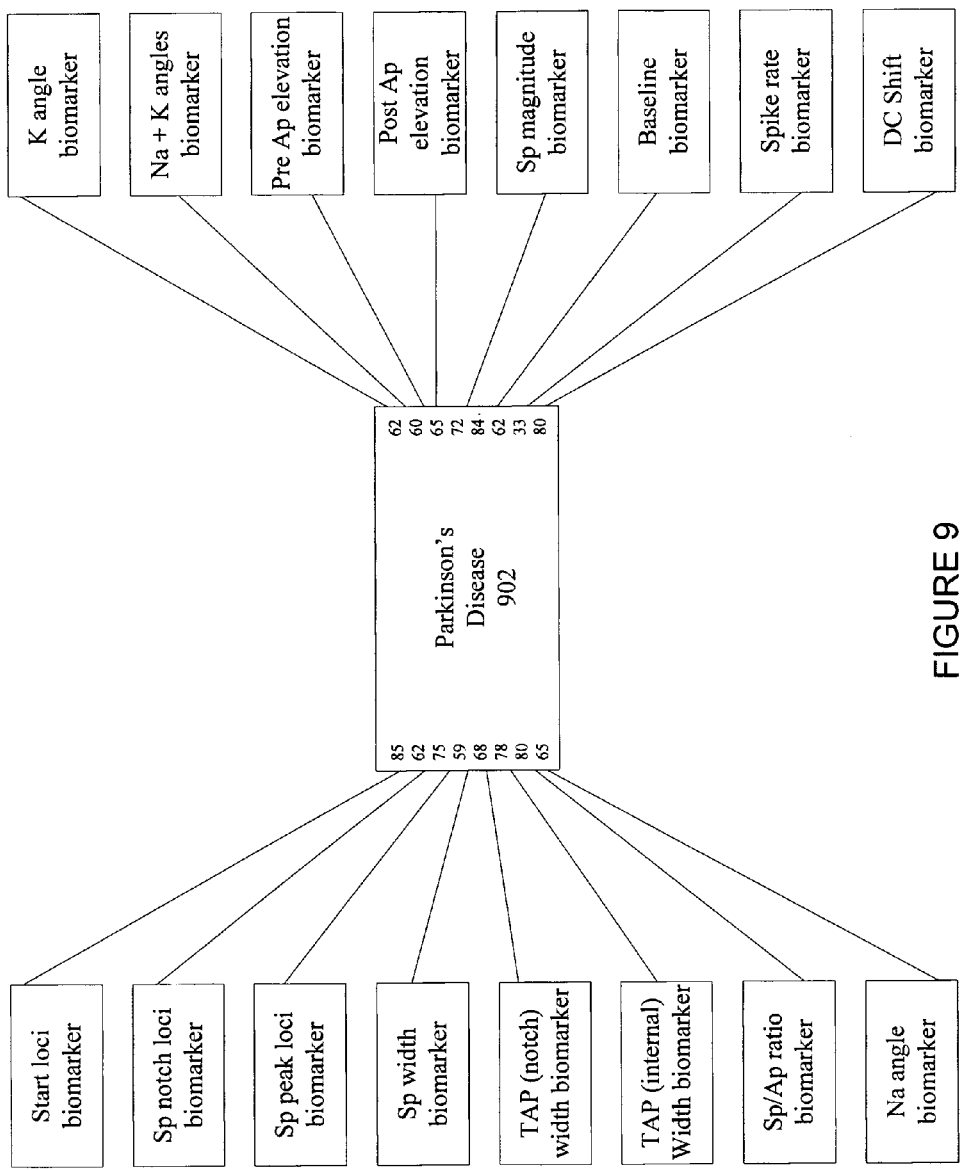
FIG. 9 is a diagram of biomarker thresholds used for indicating a disorder.

The deviation and/or similarity data obtained from the diagnostic tool 800 can then be used to generate a report indicating whether or not the patient has a disorder. For example, a pathology profile probability can be generated as a result of the data produced by the diagnostic process. For example, to indicate that a patient may have or has Parkinson's disease, the diagnostic process needs to produce deviation data for particular biomarkers that exceeds respective thresholds levels or sums. FIG. 9 is an example of the number of biomarker measures that are on average different for a patient with Parkinson's Disease when compared with biomarker measures for a normal patient or normal control measures. As shown in FIG. 9, the disorder fingerprint data for Parkinson's disease requires the 16 biomarkers to each exhibit recorded deviations for a pre-determined number of segments and tilts. For instance, the K angle biomarker would on average record approximately 62 deviations from normal, the Na and K angles biomarker on average approximately 68 deviations from normal, and the Sp/Ap ratio biomarker on average approximately 80 deviations from normal within the 630 response segments. To reduce processing time, only the best three to five biomarkers may be used to assess or determine a condition.

The system 2 is able to produce biomarker data indicating the presence of neurodegenerative disorders or diseases which are irreversible diseases where structures and functions of a part of the nervous system eg brain, spinal column and nervous pathways, break down or are destroyed by chemical, physical or biological action. Examples of neurodegenerative diseases are Multiple Sclerosis, Parkinson's Disease, Creutzveldt Jacob Disease, Schizophrenia, Huntington's Chorea, Dementia and Alzheimer's disease.

The system 2 is also able to produce biomarker data indicating the presence of neurological disorders that may or may not be irreversible but result in malfunctioning of neural functions and result in psychological and/or physiological manifestations of abnormal behavioural or physical behaviours. Such disorders include Meniere's disease, BPPV, trauma, phantom pain and clinical depression (unipolar and bipolar).

The system 2 is also able to produce biomarker data indicating the presence of drugs that may or may not have a reversible effect but result in malfunctioning of neural functions and result in psychological and/or physiological manifestations of abnormal behavioural or physical behaviours. Such disorders include the presence of alcohol (for example: 60-90 ml of 40% Alcohol/Volume), medications (SSRI's (selective serotonin reuptake inhibitors), L-dopa morning daily medication doses) and illicit drugs.

BPPV is benign positional paroxysmal vertigo, a balance disorder of the inner ear where small calcium crystals become displaced from the otolithic organs (saccule, utricle) and lodged, typically, in one of the semi circular canals. The biomarkers particularly important in producing fingerprint data and used in the diagnostic process include the Sp/Ap ratio, spike rate and DC shift. For example, as shown in FIG. 13, the DC shifts can be determined and are much smaller or not present for a patient suffering BPPV for the canal affected. The Sp/Ap plots of FIG. 12 with the significant DC effects are typical of that produced by a patient not suffering BPPV.

Meniere's disease is a balance disorder of the inner ear where the fluid in the semi-circular canals becomes more viscous and/or more copious as to change the freedom of the hair of the inner ear to react to movement. The biomarkers particularly important in producing fingerprint data and used in the diagnostic process include the Sp/Ap ratio, spike rate and DC shift, and BGi-OnBB response.

Parkinson's disease is a neurodegenerative disease affecting the basal ganglia of the brain. It is associated with the depletion of the availability of dopamine during neural functioning. Its effects on the sufferer are treated by orally administered L-dopa, an intermediate in Dopamine (neuro-transmitter) synthesis. The biomarkers are particularly important in producing fingerprint data and used in the diagnostic process include TAP (internal) from the contralateral tilt, Baseline width, spike rate, and Start point loci, and BGi-OnBB response.

Schizophrenia is a neurological disorder associated with behavioural problems of the sufferer and the presence of symptoms such as hearing voices and delusions. A sufferer can have a genetic predisposition to the disease or it can be induced from substance abuse. Excess levels of the neurotransmitter dopamine are also associated with the disorder. The biomarkers particularly important in producing fingerprint data and used in the diagnostic process include, Ap point magnitude (providing a measure of response synchrony), contralateral and ipsilateral TAP (internal), Baseline width, spike rate, Sp peak, Sp notch point loci, the Na and K angles Start point loci, and BGi-OnBB and BGi-OnAA response.

Clinical depression is a state of intense sadness, melancholia or despair that has advanced to the point of being disruptive to an individual's social functioning and/or activities of daily living. The biomarkers particularly important in producing fingerprint data and used in the diagnostic process include, contralateral and ipsilateral TAP (internal), Baseline width, spike rate, Sp peak, Sp notch point loci, the Na and K angles and Start point loci, and BGi-OnBB and BGi-OnAA response.

Huntington's Chorea is a rare hereditary disorder of the basal ganglia causing progressive motor in-coordination, abnormal involuntary movements (chorea), and intellectual decline. The biomarker data required is similar to that for Parkinson's Disease.

Alzheimer's disease is a common disease causing intellectual decline. The biomarker data required is similar to that for Parkinson's Disease.

Figure 10:
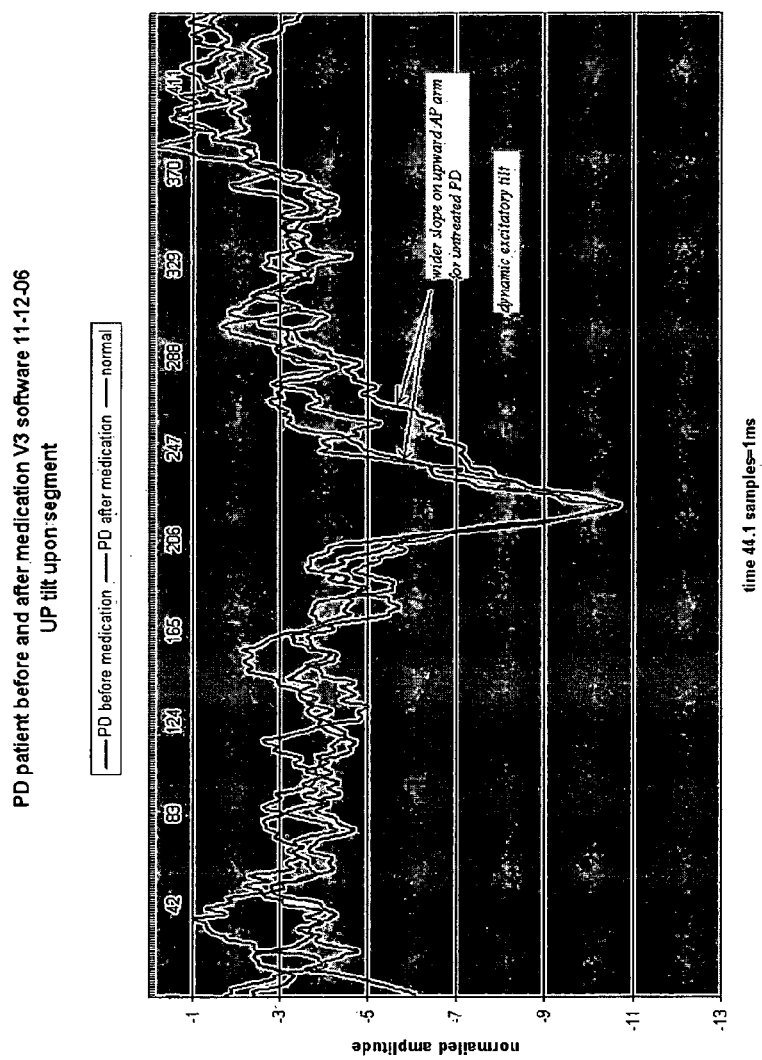
FIG. 10 is a diagram of a Sp/Ap curve generated by the system before and after the taking of a pharmaceutical compound (L-dopa) by a sufferer of Parkinson's disease.

Drug sensitivity has been tested, for example, for SSRI's (selective serotonin reuptake inhibitors) and Dopamine. When L-Dopa, i.e. Levodopa, is applied to Parkinson's disease patients the responses tend to more normal, as shown in FIG. 10, so the same fingerprint biomarkers as for Parkinson's disease are used to monitor the drug efficacy. Similarly for depression, the same fingerprint biomarkers for depression are monitored to determine the effectiveness of antidepressants (SSRI's).

Figure 11:
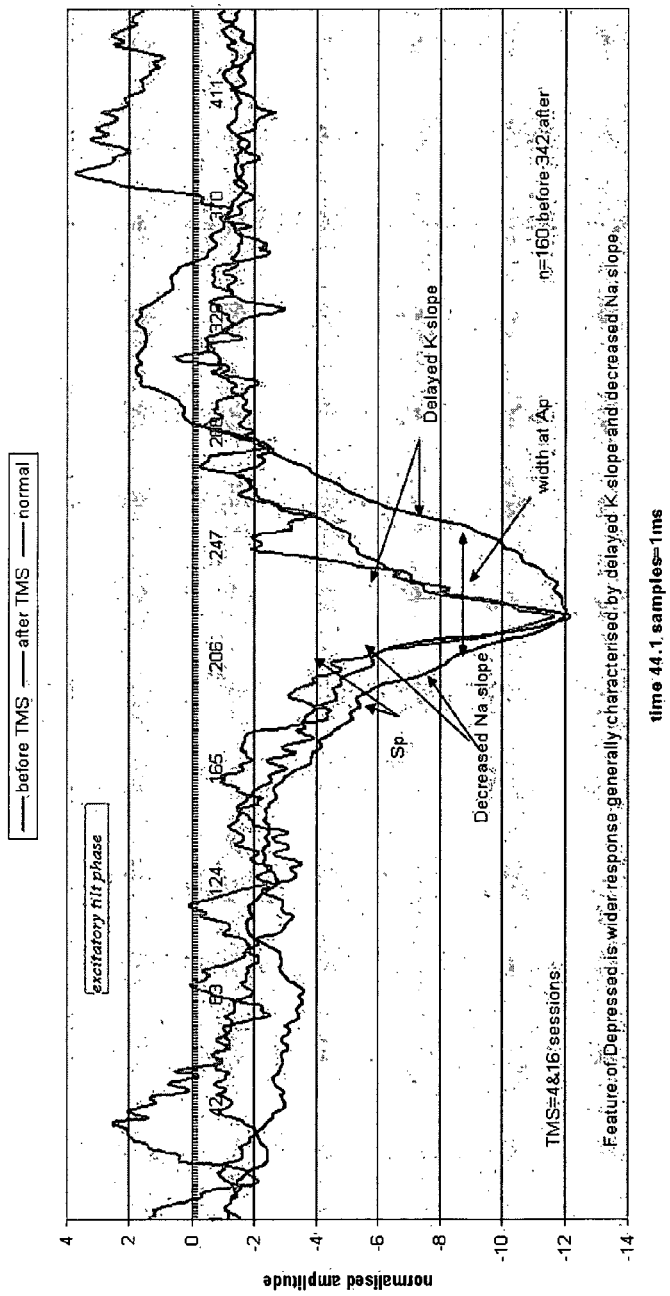
FIG. 11 is a diagram of a Sp/Ap curve generated by the system before and after exposure of a clinically depressed subject to a series of physical therapy (Transcranial Magnetic Stimulation)

Therapeutic sensitivity to physical therapy, such as transcranial magnetic stimulation (TCMS) can also be determined using the biomarker data. When TCMS has been applied to clinically depressed patients the responses tend to more normal, as shown in FIG. 11, so that changes to the same fingerprint biomarkers as for clinically depressed subjects towards a more normal profile can be used to monitor the efficacy of the TCMS therapy.

The biomarker data produced by the system 2 can also be used to determine the dynamic nature of a patient's response without reference to fingerprint biomarker data for a normal condition or a disorder. For example, the sum of the Na and K angles can be 10° different between ipsilateral and contralateral tilts (i.e. excitatory tilts and inhibitory tilts), but for a patient suffering Meniere's disease the change in the angles between the two tilts is on average much higher. Accordingly, a condition or disorder can be indicated or determined by simply observing the biomarker data obtained dynamically between different tilts.

In addition to the Na and K angle summation there are various other combinations and subsequent processing of the biomarkers measures that can be performed to provide additional biomarker data for indicating or determining a disorder or condition.

Many modifications will be apparent to those skilled in the art without departing from the scope of the present invention as herein described, with reference to the accompanying drawings.

The invention claimed is:
1. A neural response system, including:
   a plurality of different types of filters for each receiving and filtering a plurality of electrovestibulography response signals obtained from a person and generating a plurality of different types of filtered response signals based on the different types of filters;
   a segmenter for receiving the plurality of different types of filtered response signals and for segmenting the filtered response signals into time segments;
   a neural event extractor configured to receive each of the time segments and perform a neural event extraction process on each of the time segments to obtain and generate biomarker data representing a plurality of biomarkers for each segment; and
   a diagnostic tool for comparing the biomarker data of each segment with fingerprint data for a condition, and recording deviation measures between the fingerprint data and the biomarker data to determine whether said person has said condition.

2. A neural response system as claimed in claim 1, wherein the plurality of filters are arranged and configured to receive the response signals obtained from at least one electrode configured to be connected to at least one ear of the person subjected to a plurality of tilt sequences in a tilt chair.

3. A neural response system as claimed in claim 1, wherein the filters include at least one of a notch filter to substantially pass all frequencies, a first high pass filter and a second high pass filter.

4. A neural response system as claimed in claim 3, wherein the cut-off frequency for the first high pass filter is about 5 Hz and the cut-off frequency for the second high pass filter is about 120 Hz.

5. A neural response systems as claimed in claim 1, wherein the neural event extractor generates curve data representing a Sp/Ap field potential curve for each segment.

6. A neural response system as claimed in claim 5, wherein the biomarker data is determined using the curve data and the biomarkers represent relationships and constants associated with the field potential curve.

7. A neural response system as claimed in claim 5, wherein the biomarker data is determined using the curve data and the biomarkers represent spike rates, and time and voltage measurements of the field potential curve.

8. A neural response system as claimed in claim 5, wherein the biomarker data is determined using the curve data and the biomarkers represent ratios, angles and areas associated with the field potential curve.

9. A neural response system as claimed in claim 1, wherein recording the deviations includes summing the deviations, and the diagnostic tool compares sums with the fingerprint data for the biomarkers.

10. A neural response system as claimed in claim 1, wherein the biomarkers represent a comparison between a background phase and an acceleration or deceleration phase of the response signals.

11. A neural response system as claimed in claim 1, including a tilt chair for subjecting the person to a plurality of tilt sequences, and at least one electrode configured to be connected to at least one ear of the person and an amplifier circuit to record the response signals produced in response to each tilt sequence.

12. A neural response system as claimed in claim 11, wherein the tilt sequences include at least one of up/down, front/back, ipsilateral, contralateral, and rotation.

13. A neural response system as claimed in claim 12, wherein the up/down and rotation sequences includes sequences with the patient upright and sequences with the person prone.

14. A neural response system as claimed in claim 13, wherein electrodes are configured to be connected to each ear of the person to record the response signals produced in response to each tilt sequence for the left ear and the right ear.

15. A neural response system as claimed in claim 1, wherein the biomarker data indicates whether the person has at least one condition being a neurological disorder and/or neurodegenerative disease.

16. A neural response system as claimed in claim 15, wherein the condition includes one of benign positional paroxysmal vertigo (BPPV), Meniere's disease, Parkinson's disease, Schizophrenia, depression, BiPolar Affective Disorder, Alzheimers, Dementia, Attention Deficit and Hyperactivity Disorder, Multiple Sclerosis, Huntington's Chorea and Creutzfeldt Jakob disease.

17. A neural response system as claimed in claim 1, wherein the biomarker data indicates an effect arising from administration of a pharmaceutical and/or physical therapy.

18. A neural response system as claimed in claim 1, wherein the biomarker data differentiates between conditions having similar symptoms.

19. A neural response system as claimed in claim 18, wherein the conditions are benign positional paroxysmal vertigo (BPPV) and Meniere's disease.

20. A neural response system as claimed in claim 18, wherein the conditions are clinical depression and a depressive phase of a BiPolar Affective Disorder.

21. A neural response process, including:
- receiving and filtering, using a plurality of different types of filters, a plurality of electrovestibulography response signals obtained from a person to generate a plurality of different types of filtered response signals based on the different types of filters;
- receiving the different types of filtered response signals at a segmenter, and segmenting the different types of filtered response signals into time segments using the segmenter;
- receiving, at a neural event extractor, each of the time segments;
- processing, using the neural event extractor, each of the time segments to obtain and generate biomarker data representing a plurality of biomarkers for each segment; and
- comparing the biomarker data of each segment with fingerprint data for a condition, and recording deviation measures between the fingerprint data and the biomarker data to determine whether said person has said condition.

22. A neural response process as claimed in claim 21, wherein the response signals are obtained from at least one electrode connected to at least one ear of the person subjected to a plurality of tilt sequences in a tilt chair.

23. A neural response process as claimed in claim 22, wherein the tilt sequences include at least one of up/down, front/back, ipsilateral, contralateral, and rotation.

24. A neural response process as claimed in claim 23, wherein the up/down and rotation sequences includes sequences with the person upright and sequences with the person prone.

25. A neural response process as claimed in claim 24, including connecting electrodes to each ear of the person to record the response signals produced in response to each tilt sequence for the left ear and the right ear.

26. A neural response process as claimed in claim 21, wherein the filters include at least one of a notch filter to substantially pass all frequencies, a first high pass filter and a second high pass filter.

27. A neural response process as claimed in claim 26, wherein the cut-off frequency for the first high pass filter is about 5 Hz and the cut-off frequency for the second high pass filter is about 120 Hz.

28. A neural response process as claimed in claim 21, wherein said processing generates curve data representing a Sp/Ap field potential curve for each segment.

29. A neural response process as claimed in claim 28, wherein the biomarker data is determined using the curve data and the biomarkers represent relationships and constants associated with the field potential curve.

30. A neural response process as claimed in claim 28, wherein the biomarker data is determined using the curve data and the biomarkers represent spike rates, and time and voltage measurements of the field potential curve.

31. A neural response process as claimed in claim 28, wherein the biomarker data is determined using the curve data and the biomarkers represent ratios, angles and areas associated with the field potential curve.

32. A neural response process as claimed in claim 21, wherein recording the deviations includes summing the deviations, and the sums are compared with the fingerprint data for the biomarkers.

33. A neural response process as claimed in claim 21, wherein the biomarkers represent a comparison between a background phase and an acceleration or deceleration phase of the response signals.

34. A neural response process as claimed in claim 21, wherein the biomarker data indicates whether the person has at least one condition being a neurological disorder and/or neurodegenerative disease.

35. A neural response process as claimed in claim 34, wherein the condition includes one of benign positional paroxysmal vertigo (BPPV), Meniere's disease, Parkinson's disease, Schizophrenia, depression, BiPolar Affective Disorder, Alzheimers, Dementia, Attention Deficit and Hyperactivity Disorder, Multiple Sclerosis, Huntingdon's Chorea and Creutzfeldt Jakob disease.

36. A neural response process as claimed in claim 21, wherein the biomarker data indicates an effect arising from administration of a pharmaceutical and/or physical therapy.

37. A neural response process as claimed in claim 21, wherein the biomarker data is used to differentiate a diagnosis between conditions having similar symptoms.

38. A neural response process as claimed in claim 37, wherein the conditions are benign positional paroxysmal vertigo (BPPV) and Meniere's disease.

39. A neural response process as claimed in claim 37, wherein the conditions are clinical depression and a depressive phase of a BiPolar Affective Disorder.

* * * * *